US012558568B2

(12) United States Patent
Broad

(10) Patent No.: US 12,558,568 B2
(45) Date of Patent: Feb. 24, 2026

(54) LEAF ACTUATOR FOR A MULTI-LEAF COLLIMATOR

(71) Applicant: Elekta Limited, Crawley (GB)

(72) Inventor: Martin Broad, Crawley (GB)

(73) Assignee: Elekta Limited, Crawley (GB)

( * ) Notice: Subject to any disclaimer, the term of this patent is extended or adjusted under 35 U.S.C. 154(b) by 332 days.

(21) Appl. No.: 17/906,153

(22) PCT Filed: Mar. 11, 2021

(86) PCT No.: PCT/EP2021/056276
§ 371 (c)(1),
(2) Date: Sep. 12, 2022

(87) PCT Pub. No.: WO2021/180901
PCT Pub. Date: Sep. 16, 2021

(65) Prior Publication Data
US 2023/0100438 A1     Mar. 30, 2023

(30) Foreign Application Priority Data
Mar. 13, 2020    (GB) ...................................... 2003688

(51) Int. Cl.
*A61N 5/10*          (2006.01)

(52) U.S. Cl.
CPC ......... *A61N 5/1045* (2013.01); *A61N 5/1048* (2013.01)

(58) Field of Classification Search
CPC .. A61N 5/1042; A61N 5/1045; A61N 5/1048; A61N 5/1047; G21K 1/046; G21K 1/04; G21K 1/043
See application file for complete search history.

(56) References Cited

U.S. PATENT DOCUMENTS

| | | | |
|---|---|---|---|
| 6,459,769 | B1 | 10/2002 | Cosman |
| 7,085,355 | B1 | 8/2006 | Albagli et al. |

(Continued)

FOREIGN PATENT DOCUMENTS

| | | |
|---|---|---|
| CN | 201226257 Y | 4/2009 |
| CN | 202128818 U | 2/2012 |

(Continued)

OTHER PUBLICATIONS

Machine translation of CN-107929955 (Year: 2018).*

(Continued)

*Primary Examiner* — David J Makiya
*Assistant Examiner* — Soorena Kefayati
(74) *Attorney, Agent, or Firm* — Schwegman Lundberg & Woessner, P.A.

(57) ABSTRACT

A leaf unit for a multi-leaf collimator may comprise a leaf, a leaf actuator screw, a rotatable part threadably engaged with the leaf actuator screw, a leaf actuator motor, and a supporting bracket. The leaf actuator screw including a first end fixedly attached to the leaf and the leaf actuator motor being coupled to the rotatable part. The support bracket comprising a first portion with a first opening arranged to receive and support the leaf actuator motor and a second portion with a second opening including a bearing. The second opening being arranged to receive and support the rotatable part. A center of the first opening is aligned with that of the second opening so that an axis of the leaf actuator motor and an axis of the rotatable part of each leaf actuator are colinear.

14 Claims, 3 Drawing Sheets

(56) References Cited

U.S. PATENT DOCUMENTS

| | | | | |
|---|---|---|---|---|
| 7,167,542 | B2 * | 1/2007 | Juschka | G21K 1/046 |
| | | | | 378/150 |
| 8,384,049 | B1 | 2/2013 | Broad | |
| 8,718,234 | B2 * | 5/2014 | Echner | A61N 5/1045 |
| | | | | 378/152 |
| 10,857,385 | B2 * | 12/2020 | Xiao | A61N 5/1045 |
| 12,138,482 | B2 | 11/2024 | Broad | |
| 12,186,589 | B2 | 1/2025 | Broad | |
| 2002/0101959 | A1 | 8/2002 | Kato et al. | |
| 2006/0067480 | A1 * | 3/2006 | Juschka | G21K 1/046 |
| | | | | 378/150 |
| 2006/0193441 | A1 | 8/2006 | Cadman | |
| 2009/0147917 | A1 * | 6/2009 | Mohr | G21K 1/04 |
| | | | | 378/65 |
| 2009/0262901 | A1 | 10/2009 | Broad et al. | |
| 2011/0026683 | A1 * | 2/2011 | Broad | A61N 5/1045 |
| | | | | 378/152 |
| 2011/0199085 | A1 | 8/2011 | Allen et al. | |
| 2012/0076269 | A1 | 3/2012 | Roberts | |
| 2013/0000428 | A1 * | 1/2013 | Ji | A61N 5/1045 |
| | | | | 74/30 |
| 2015/0170778 | A1 * | 6/2015 | Echner | A61N 5/1045 |
| | | | | 250/505.1 |
| 2017/0087386 | A1 | 3/2017 | Mellenberg et al. | |
| 2017/0128746 | A1 * | 5/2017 | Zwart | A61N 5/1077 |
| 2017/0148536 | A1 | 5/2017 | Kawrykow et al. | |
| 2018/0012676 | A1 * | 1/2018 | Xu | G21K 1/046 |
| 2018/0035969 | A1 * | 2/2018 | Jin | G21K 1/046 |
| 2018/0161602 | A1 | 6/2018 | Kawrykow et al. | |
| 2019/0001153 | A1 * | 1/2019 | Jones | H05H 13/02 |
| 2019/0054316 | A1 * | 2/2019 | Sheng | A61N 5/1036 |
| 2020/0185119 | A1 * | 6/2020 | Stahl | A61N 5/1045 |
| 2020/0304045 | A1 * | 9/2020 | Ye | H02P 25/064 |
| 2021/0187322 | A1 * | 6/2021 | Zhong | G21K 1/046 |
| 2021/0290979 | A1 | 9/2021 | Liu et al. | |
| 2023/0101881 | A1 | 3/2023 | Broad | |
| 2023/0110626 | A1 | 4/2023 | Broad | |
| 2023/0113879 | A1 | 4/2023 | Broad | |
| 2023/0173304 | A1 | 6/2023 | Broad | |

FOREIGN PATENT DOCUMENTS

| | | | | |
|---|---|---|---|---|
| CN | 204502129 | U | 7/2015 | |
| CN | 205460495 | U | 8/2016 | |
| CN | 205656865 | U | 10/2016 | |
| CN | 205843700 | U | 12/2016 | |
| CN | 107929955 | A * | 4/2018 | A61N 5/1048 |
| CN | 110538387 | A | 12/2019 | |
| DE | 3030332 | A1 | 2/1982 | |
| EP | 0314214 | A2 | 5/1989 | |
| EP | 3053628 | A1 | 8/2016 | |
| EP | 3266501 | A1 | 1/2018 | |
| GB | 2423909 | | 9/2006 | |
| JP | 2006081585 | A | 3/2006 | |
| JP | 2008206563 | A | 9/2008 | |
| WO | WO-2008076035 | A1 | 6/2008 | |

OTHER PUBLICATIONS

Translation of CN-107929955-A (Year: 2018).*

"International Application Serial No. PCT/EP2021/056276, International Search Report dated Jun. 17, 2021", (Jun. 17, 2021), 3 pgs.

"International Application Serial No. PCT/EP2021/056276, Written Opinion dated Jun. 17, 2021", (Jun. 17, 2021), 5 pgs.

"United Kingdom Application Serial No. 2003688.5, Examination Report dated Aug. 14, 2020", (Aug. 14, 2020), 6 pgs.

"U.S. Appl. No. 17/906,147 Preliminary Amendment Filed with Application", 8 pgs.

"U.S. Appl. No. 17/906,149 Preliminary Amendment Filed with Application", 7 pgs.

"International Application Serial No. PCT/EP2021/056270, International Search Report dated Jun. 17, 2021", (Jun. 17, 2021), 3 pgs.

"International Application Serial No. PCT/EP2021/056270, Written Opinion dated Jun. 17, 2021", (Jun. 17, 2021), 5 pgs.

"International Application Serial No. PCT/EP2021/056278, International Search Report dated Jun. 16, 2021", (Jun. 16, 2021), 3 pgs.

"International Application Serial No. PCT/EP2021/056278, Written Opinion dated Jun. 16, 2021", (Jun. 16, 2021), 6 pgs.

"International Application Serial No. PCT/EP2021/056281, International Search Report dated Jun. 16, 2021", (Jun. 16, 2021), 3 pgs.

"International Application Serial No. PCT/EP2021/056281, Written Opinion dated Jun. 16, 2021", (Jun. 16, 2021), 5 pgs.

"International Application Serial No. PCT/EP2021/056282, International Search Report dated Jun. 16, 2021", (Jun. 16, 2021), 3 pgs.

"International Application Serial No. PCT/EP2021/056282, Written Opinion dated Jun. 16, 2021", (Jun. 16, 2021), 5 pgs.

"United Kingdom Application Serial No. 2003664.6, Examination Report dated Aug. 13, 2020" (Aug. 13, 2020), 7 pgs.

"United Kingdom Application Serial No. 2003673.7, Examination Report dated Sep. 15, 2020", (Sep. 15, 2020), 6 pgs.

"United Kingdom Application Serial No. 2003679.4, Examination Report dated Sep. 15, 2020" (Sep. 15, 2020), 8 pgs.

"United Kingdom Application Serial No. 2003694.3, Combined Search and Examination Report mailed Sep. 15, 2020", 7 pgs.

"U.S. Appl. No. 17/906,149, Non Final Office Action mailed Jun. 18, 2024", 12 pgs.

"U.S. Appl. No. 17/906,181, Non Final Office Action mailed Jul. 5, 2024", 9 pgs.

Translation of JP2008206563A (2008) from U.S. Appl. No. 17/906,181 Non Final Office Action mailed Jul. 5, 2024, 10 pages.

Translation of CN-202128818-U (2012) from U.S. Appl. No. 17/906,181 Non Final Office Action mailed Jul. 5, 2024, 3 pages.

"U.S. Appl. No. 17/906,147, Notice of Allowance mailed Jul. 12, 2024", 8 pgs.

"U.S. Appl. No. 17/906,147, Corrected Notice of Allowability mailed Aug. 1, 2024", 2 pgs.

"U.S. Appl. No. 17/906,149, Response filed Aug. 20, 2024 to Non Final Office Action mailed Jun. 18, 2024", 7 pgs.

"U.S. Appl. No. 17/906,149, Notice of Allowance mailed Sep. 6, 2024", 7 pgs.

"U.S. Appl. No. 17/906,181, Response filed Oct. 7, 2024 to Non Final Office Action mailed Jul. 5, 2024", 11 pgs.

"U.S. Appl. No. 17/906,179, Notice of Allowance mailed Nov. 1, 2024", 7 pgs.

"U.S. Appl. No. 17/906,149, PTO Response to Rule 312 Communication mailed Nov. 15, 2024", 2 pgs.

"U.S. Appl. No. 17/906,179, Corrected Notice of Allowability mailed Nov. 15, 2024", 2 pgs.

"U.S. Appl. No. 17/906,181, Notice of Allowance mailed Nov. 27, 2024", 8 pgs.

"U.S. Appl. No. 17/906,181, Corrected Notice of Allowability mailed Dec. 13, 2024", 3 pgs.

"Chinese Application No. 202180034981.X, Office Action dated Sep. 25, 2025", (Sep. 25, 2025), 14 pgs.

"European Application No. 21 712 463.5, Examination Report dated Nov. 29, 2024", (Nov. 29, 2024), 3 pgs.

* cited by examiner

LEAF ACTUATOR FOR A MULTI-LEAF COLLIMATOR

PRIORITY APPLICATIONS

This application is a U.S. National Stage Filing under 35 U.S.C. § 371 from International Application No. PCT/EP2021/056276, filed on Mar. 11, 2021, and published as WO2021/180901 on Sep. 16, 2021, which claims the benefit of priority to United Kingdom Application No. 2003688.5, filed on Mar. 13, 2020; the benefit of priority of each of which is hereby claimed herein, and which applications and publication are hereby incorporated herein by reference in their entireties.

FIELD

The present disclosure relates to a leaf actuator for a multi-leaf collimator, and a multi-leaf collimator comprising the same.

BACKGROUND

Radiotherapeutic apparatus involves the production of a beam of ionising radiation, usually x-rays or a beam of electrons or other sub-atomic particles. This is directed towards a cancerous region of a patient (e.g. a tumour), and adversely affects the cancerous cells, thereby reducing the prevalence thereof. The beam is delimited so that the radiation dose is maximised in the cancerous cells and minimised in healthy cells of the patient, as this improves the efficiency of treatment and reduces the side effects in a patient.

In a radiotherapy apparatus the beam can be delimited using a beam limiting device such as a 'multi-leaf collimator' (MLC). This is a collimator which consists of a large number of elongate thin leaves arranged side by side in an array. The leaves are usually made from a high atomic numbered material, usually tungsten, so that they are substantially opaque to the radiation.

Each leaf is moveable longitudinally so that its tip, or leading edge, can be extended into or withdrawn from the radiation beam. All the leaves can be withdrawn to allow the radiation beam to pass through, or all the leaves can be extended so as to block the radiation beam completely. Alternatively, some leaves can be withdrawn and some extended so as to define any desired shape, within operational limits. The array of leaf tips can thus be positioned so as to define a variable edge to the collimator. A multi-leaf collimator usually consists of two banks of such arrays (i.e. leaf banks), each leaf bank projecting into the radiation beam from opposite sides of the collimator. The variable edges provided by the two leaf banks thus collimate the radiation beam to a chosen cross-sectional shape, usually that of a target tumour volume to be irradiated. That is, the two leaf banks combine to provide an aperture of variable shape for shaping the radiation beam.

The individual leaves may be moved independently of each other out to define the shape of the radiation beam by defining the shape of the aperture. In some cases, the leaves are moved in unison to define the position of the radiation beam by defining the position of the aperture. In use, the shape and/or position of the aperture may need to be changed quickly. For example, in some applications, MRI imaging of the treated subject is carried out in real time to track the position of a tumour to be irradiated by the radiotherapy device. In this case, the silhouette of the tumour from the perspective of the direction of travel of the radiation beam may change, for example owing to movement of the patient (e.g. due to breathing) during treatment. The shape and position of the multi-leaf collimator aperture can be changed so that the shape and position of the radiation beam tracks the changing shape and/or position of the tumour silhouette. Thus, the beam consistently irradiates as much of the tumour as possible while irradiating as little as possible of the surrounding healthy tissue, even when the tumour moves.

The speed of movement of the individual leaves is important in ensuring that the change in shape and/or position of the aperture keeps up with the changing shape and/or position of the tumour silhouette. The leaf actuators (i.e. the means for moving the individual leaves) play an important role in achieving suitable leaf speeds. However, the form and mechanism of the leaf actuators govern not only the speed, but also the accuracy of positioning of the individual leaves, and the stability and durability of the leaf actuators themselves. Often, there is a trade-off between speed on one hand and accuracy of positioning, stability and/or durability on the other.

It is desirable to provide an accurate leaf actuator having high speed, high durability and high stability.

SUMMARY

Aspects and features of the present invention are set out in the accompanying claims.

BRIEF DESCRIPTION OF THE DRAWINGS

Specific embodiments are described below by way of example only and with reference to the accompanying drawings in which.

DETAILED DESCRIPTION OF EMBODIMENTS

Multi-Leaf Collimator

A multi-leaf collimator includes a leaf bank including a plurality of leaves. The leaves are individually moveable longitudinally within the leaf bank so that they can project into and out of the path of a radiation beam. A multi-leaf collimator may have two opposing leaf banks, wherein the radiation beam passes through an aperture between the banks.

Each leaf is configured to attenuate radiation. The leaves of the multi-leaf collimator define the shape of the aperture. The leaves are plate-like structures arranged side-by-side in a stack, much like playing cards in a deck of cards. The leaves can slide against each other and move independently of each other so that the 'deck' (i.e. the leaf bank) when viewed from the side has an outline at the ends which is defined by the position of the 'cards' (i.e. the leaves) relative to each other. Part of the radiation beam is blocked by the leaf bank so that the beam takes on a shape which is the same as the outline defined by the position of the leaves.

The leaves may be substantially rectilinear in shape in the plane thereof. The leaves are relatively thin in a direction perpendicular to both the direction of the axis of the beam and plane of the leaves, allowing a high-resolution aperture shape to be obtained. The leaves are relatively deep in the direction of the axis of the radiation beam in order to render them sufficiently opaque at X-ray wavelengths/energies. The leaves are relatively elongate (relatively long in the direction perpendicular to their thickness and depth), allowing them to adopt a wide range of positions while maintaining contact with the leaf guides. The leaves comprise a dense material (high atomic number material), such as tungsten, which is capable of absorbing and/or scattering X-rays. A leaf actuator causes an individual leaf to move relative to other leaves in the leaf bank.

Figure 1:
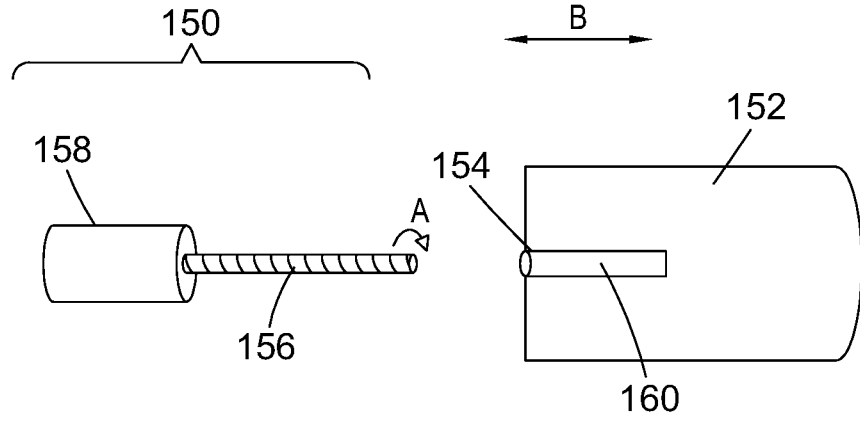
FIG. 1 shows a multi-leaf collimator leaf unit assembly according to the prior art.

FIG. 1 shows a leaf 152 of a multi-leaf collimator and a leaf actuator drive 150 for moving the leaf 152. The leaf 152 and leaf actuator drive 150 are known herein as a "leaf unit".

In a leaf bank comprising a plurality of leaves 152, each leaf will have a respective leaf actuator drive 150. Each leaf actuator 154 is arranged to drive a respective leaf so that the leaves 152 can be moved in their respective leaf banks independently of each other. That is, each leaf actuator 154 is arranged to engender relative linear motion between one leaf 152 and the other leaves in the leaf bank.

The leaf actuator 154 includes a leaf actuator motor 158. A suitable controller will typically be provided (not shown), which is arranged to provide signals to the leaf actuator motor 158 in order to move the appropriate leaf or leaves 152 to provide the required shape or position of the aperture. All leaves can be driven in unison or individually. A control system suitable for monitoring and controlling the position of the leaves ensures that collisions between leaves of opposing leaf banks are avoided. The movement of the leaves may be carried out define the shape of the aperture (and hence the radiation beam) or to move the shaped aperture provided by the leaves relative to the axis of the radiation beam.

In known systems the leaf actuators may each comprise a leaf actuator screw 156 (e.g. a rotatable threaded rod such as one appropriate for an acme screw, ball screw or lead screw assembly). The leaves 152 themselves are coupled as a load to the end of the leaf actuator screw 156. The leaf actuator motor 158 driving the leaf actuator screw may be a DC, DC servo, DC brushless, DC brushless servo, AC, AC servo, or stepper motor. The leaf actuator motor is coupled to the leaf actuator screw 156 at the opposite end of the leaf actuator screw to the end coupled to the leaf 152.

In known systems the leaf 152 is coupled to the actuator screw with a threaded nut 154. The nut 154 is threadably engaged with the leaf actuator screw 156. The nut 154 is fixedly attached to the leaf 152 so that rotational of the nut around its axis causes corresponding rotation of the leaf That is, the nut is rotationally fixed relative to the leaf.

The leaf tail (the portion of the leaf 152 at the end of the leaf furthest from the leaf tip) may have an inset area to accommodate parts of the leaf actuator 154. The nut 154 comprises an elongate aperture 160 in the leaf tail running along a substantial portion of the length of the leaf. The elongate aperture 160 is accessible to the leaf actuator screw 156 via an internally threaded section of the nut which engages with the leaf actuator screw 156.

When multiple leaves are arranged in a bank in a multi-leaf collimator, the other leaves in the leaf bank rotationally limit the movement of the leaf 152 but allow linear movement of the leaf 152 in the plane of the leaf. In use the leaf actuator screw 156 is rotated by the leaf actuator motor 158 shown by arrow A. The leaf actuator screw 156 is threadably engaged with the nut 154. However, the nut does not rotate with the leaf actuator screw, because the leaf tail rotationally limits the movement of the nut. Instead the leaf actuator screw 156 interacts with the threaded section in the leaf tail to cause the rotational motion of the leaf actuator screw to be converted into the linear motion of the threaded section and hence the leaf. Rotation of the leaf actuator screw 158 drives the threaded section, and hence the leaf, in the direction parallel to the leaf actuator screw axis and in the plane of the leaf shown by arrow B.

The stroke of the leaf actuator 154 may be sufficient to allow the leading edge of the leaf to be extended at least half way into the path of the radiation beam and also retract so that it is clear of the path of the radiation beam. The stroke may therefore be between about one half and about two times the diameter of the radiation beam for which the multi-leaf collimator is designed. The stroke may be between about one quarter the length of one leaf to about the length of one leaf.

It is noted that in FIG. 1 for illustrative purposes the leaf 152 and the leaf actuator screw 156 are shown de-coupled. In use, the leaf actuator screw 156 is threadably engaged with the nut 154 on the leaf 152.

Known systems use a leaf actuator screw for converting motor torque to linear motion to actuate a leaf. However, these systems have certain limitations.

Trade-Off Between Speed and Accuracy in Conventional Leaf Actuators

The linear speed of the leaf 152 is dependent on the leaf actuator screw 156 pitch and the angular speed of rotation the leaf actuator screw 156. A leaf speed of greater than 5 cm/s is desirable when the multi-leaf collimator is operating in real time to track the tumour silhouette.

A high leaf speed can be achieved in two different ways: rotating the leaf actuator screw with a high rpm; or producing a leaf actuator screw with a large pitch. The leaf actuator screws are leadscrews of the motor.

A large pitch provides greater efficiency in leadscrews. However, a leadscrew with a large pitch involves a number of drawbacks. Leadscrews having a large pitch generally have multi-start threads and have a high helix angle to achieve a large linear displacement of a nut per full rotation of the leadscrew. However, if the efficiency of the leadscrew exceeds 50% it is likely that the actuator will overhaul or back drive. Further, high screw pitch is undesirable in a multi-leaf collimator as it would mean that, at gantry positions in which the leaves are driven against gravity, the leaves may lose position once power is removed from the leaf actuators motors. In addition, is more difficult to accurately position a component when using a high-pitch leaf actuator screw as the control system can "overshoot" the desired position.

Leadscrews with a lower pitch generally have a lower tendency to back drive, are self-locking to a degree and facilitate more accurate positioning with less control system input. However, a leadscrew having a lower pitch has a lower efficiency. To achieve a high linear speed, a leadscrew having a lower pitch needs to be rotated with a greater rotational speed. When rotating leadscrews with a high length to diameter ratio, as leaf actuator screws often have since they are designed to fit within a single leaf-width, there is a critical rotational speed. When a leadscrew reaches its critical speed, it begins to vibrate to an unacceptable degree. This increases wear (which reduces component life), increases noise and reduces efficiency.

The critical speed in a known leaf actuator is constrained due to a number of factors, and the screw cannot be rotated above this limit without causing damage, and maximum possible linear speed of the leaf without causing damage due to vibration is limited.

The critical speed is dependent on leaf actuator screw length, diameter and support bearing configuration.

The leaf width (or pitch between the leaves) dictates the space available for parts of the leaf actuator. For example, the diameter of the leaf actuator screw 156 is limited to the mechanical width of the leaf 152. The length of the leaf actuator screw 156 is chosen in accordance with the leaf travel required for the particular multi-leaf collimator or its application. The support bearing configuration is also limited, since in known leaf actuators it is not possible to support the end of the leaf actuator screw which must be free to allow relative linear motion between the leaf actuator screw and the leaf.

Owing to the above constraints, the critical speed (in rpm) of the known leaf drive screws is limited, and the screw cannot be rotated above this limit without causes damage. Therefore, in the leaf actuator design is also limited in terms of the maximum possible linear speed of the leaf before vibration levels increase to an unacceptable level.

New Leaf Actuator

According to an implementation of the disclosure there is provided a leaf unit incorporating a leaf actuator having a leaf actuator screw which is not rotatable relative to the leaf, as described below.

The leaf unit has an actuator which relies on having a leaf actuator screw which cannot rotate or move in a linear fashion relative to the leaf. This may be achieved by rigidly attaching the leaf actuator screw to the rear of the leaf so that it is not able to rotate. Instead of rotating the leaf actuator screw to cause the leaf to move in a linear fashion, the leaf actuator motor rotates another component which engages with the thread on the leaf actuator screw and pushes or pulls the leaf actuator screw relative to the component so that the leaf actuator screw moves together with the leaf. Thus, the function of the leaf actuator screw is to provide linear motion only, i.e. to push and pull the leaf.

In a preferred arrangement, the leaf actuator screw is coupled at one end thereof to the leaf (e.g. the leaf tail) so that it cannot rotate relative to the leaf. A nut, or other rotatable part (e.g. a worm), engaged with the thread on the leaf actuator screw is arranged to be rotated by the leaf actuator motor such that the leadscrew, and hence the leaf, moves in a linear motion relative to the nut. Thus, as the motor rotates the nut, the leaf actuator screw and the leaf are driven in a linear motion so that the leading edge of the leaf moves into and out of the path of the radiation beam. The nut (e.g. leaf actuator screw nut), which in the rotating leaf actuator screw leaf actuator design would be coupled to the leaf tail, is now mounted in the end of a rotatable tube. The tube is then coupled to the motor and gearbox assembly. The length of the tube is sufficiently long that the leaf actuator screw can be withdrawn within its length.

Figure 2:
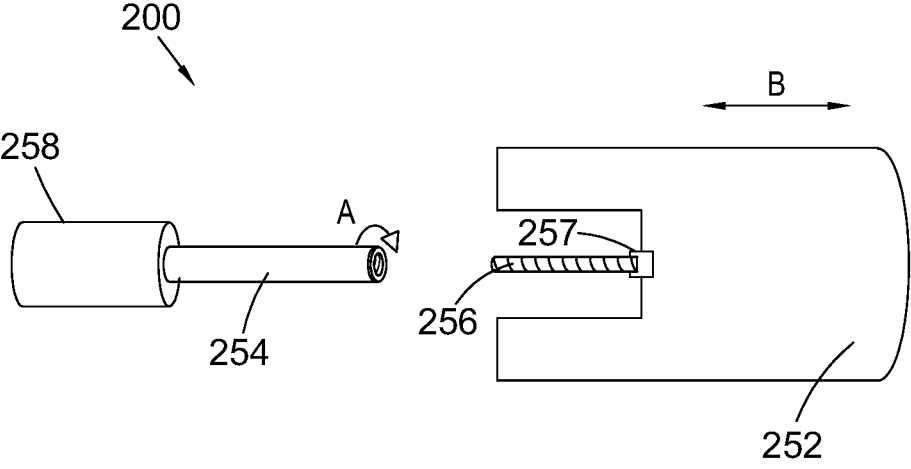
FIG. 2 shows a multi-leaf collimator leaf unit according to an embodiment.

FIG. 2 illustrates an implementation of the present disclosure. A leaf unit 200 includes a leaf 252 and a leaf actuator 250. The leaf actuator includes a leaf actuator screw 256 (e.g. one suitable for a lead screw arrangement), a leaf actuator motor 258, and a rotatable part 254. The leaf actuator screw 256 is coupled at a first end thereof to the leaf tail via a coupling part 257. The coupling part 257 comprises a small plate or shim with a first receiving portion arranged to receive the first end of the leaf actuator screw 256 and a second receiving portion arranged to receive a protrusion on the leaf 252. The leaf actuator screw comprises external threading.

A portion of the leaf actuator screw 256 distal from the first end is inserted into a rotatable part 262 comprising a tube or sleeve. When the leaf actuator is inserted into the rotatable part the rotatable part envelops a section of the leaf actuator screw 256. The rotatable part 254 includes a threaded part on an interior surface thereof to be engaged with at least a part of the distal portion of the leaf actuator screw 256. The rotatable part 254 is rotatable around the axis of the leaf actuator screw 256 by the leaf actuator motor 258. The leaf actuator screw 256 is not rotatable around its own axis due to its coupling at the first end to the leaf tail.

In operation, the leaf actuator motor 258 rotates the rotatable part 254 around the axis of the leaf actuator screw 256, shown by arrow A. The threaded section on the internal surface of the rotatable part 254 acts to translate the relative rotational motion between the rotatable part 254 and the leaf actuator screw 256 into relative linear motion between the rotatable part 254 and the leaf actuator screw 256. The leaf actuator screw 256 applies a force to the leaf 252 and the leaf 252 moves together with the leaf actuator screw 256 in a linear motion relative to the rotatable part 254 and the leaf actuator motor 258.

In FIG. 2 for illustrative purposes the leaf 252 and the rotatable part 254 are shown de-coupled. In use the rotatable part 254 is threadably engaged with the leaf actuator screw 256 on the leaf 252.

Figure 3:
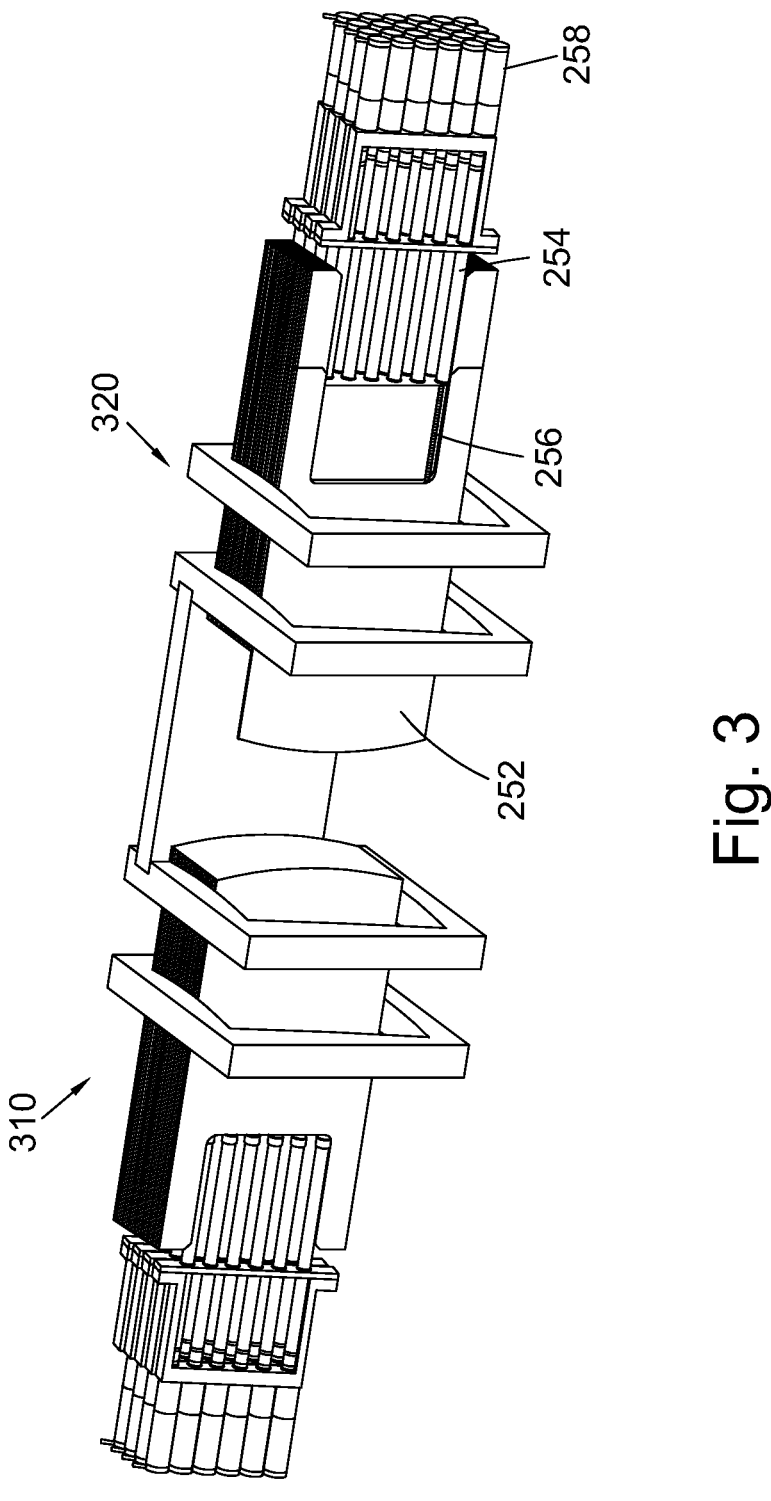
FIG. 3 shows a multi-leaf collimator according to an implementation.

FIG. 3 shows a multi-leaf collimator according to an implementation. The multi-leaf collimator includes a first bank of leaves 310 and a second bank of leaves 320, the two leaf banks being opposed about an aperture. A leaf 252 in the second bank of leaves is in the fully extended position. This can be seen by the alignment between the tips of the leaves—the tip of the leaf 252 protrudes into the aperture between the two leaf banks. The tip of leaf 252 extend further into the aperture than any other leaves in the second leaf bank 320, which are all aligned and in the retracted position. The leaves in the first leaf bank 310 are all retracted and aligned.

As shown for leaf 252, in a fully extended state, the majority of the length of the leaf actuator screw 256 is outside of the rotatable part 254, with the end of the thread of the leaf actuator screw 256 most distal from the first end is still being engaged with the threaded part of the rotatable part 254. In this state, the distance between the rotatable part 254 and the leaf 252 is maximal. In a fully retracted state, the majority of the length of the leaf actuator screw 256 is inside the rotatable part 254 and the distance between the leaf 252 and the rotatable part 254 is minimal.

In FIG. 3, leaf 252 is in the fully extended position, and the leadscrew 256 is visible and not enveloped by the rotatable part 258. Leaf 352 in the opposing bank is in the fully retracted state and the leadscrew is fully enveloped by the rotatable part such that the leadscrew is not visible in FIG. 3.

In a specific example, the aperture of a multi-leaf collimator is at Iso centre of 5 mm. The multi-leaf collimator has 160 leaves and the leaf width is approx. 1.7-2 mm wide. The leaf travel is approximately 100 mm. In this example, the leaf actuator screws are no more than 2 mm in diameter and at least 100 mm long.

Figure 4:
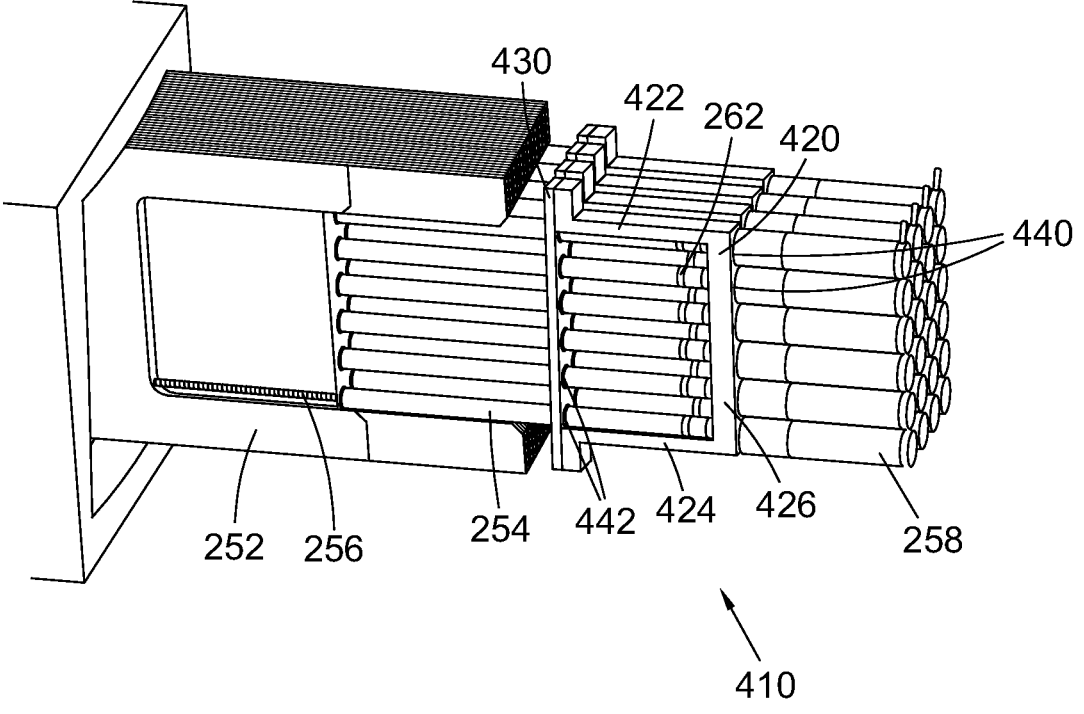
FIG. 4 shows a view of the multi-leaf collimator of FIG. 3.

As shown in FIG. 4 a series of six leaf actuators are mounted in a square-shaped bracket 410.

The bracket 410 includes a first bracket portion 420 having two arms 422, 424 and an elongate plate portion 426 provided between the two arms so as to form a U shape making up three sides of the square shape of the bracket 410. The elongate plate portion 426 has a series 440 of six through holes therein, each through hole of the first series 440 dimensioned so as to receive and support a leaf actuator motor 258. The first bracket portion 420 holds each leaf actuator motor 258 by its motor casing by applying a torque resistance to prevent rotation of the motor casing relative to the first bracket. The first bracket portion 420 also applies a linear force resistance to the motor casing in the direction of the axis of the leaf actuator motor 258 to prevent linear movement of the motor casing relative to the first bracket portion 420.

The bracket also includes a second bracket portion 430 which is provided between the ends of the two arms 422, 424 so as to create the square shape of the bracket 410. The second bracket portion 430 is an elongate plate having second series 442 of six through holes therein, the through holes each having a bearing therein arranged to receive and support a respective tube (rotatable part 254) of the leaf actuators. Advantageously, the shape of the bracket 270 provides a light, yet stable, support for the leaf actuators mounted therein. Further advantageously, the bracket provides stability for the rotatable parts especially at high rotational speeds, which increases the maximum possible critical speed and hence the maximum possible efficiency of the rotatable parts 254. The bracket also helps to reduce noise and vibration of the rotatable part 254 at all speeds, more so at high speeds.

The respective centres of the first series 440 of through holes are aligned with those of the second series 442 of through holes so that the axes of the leaf actuator motor 258 and rotatable part 424 of each leaf actuator are collinear when the leaf actuators are mounted in the bracket 410. When incorporated into the leaf unit, the second bracket portion 430 is positioned nearer the leaf tail than the elongate plate portion 426 of the first bracket portion 420. The first bracket portion 420 is removably coupled to the second bracket portion 430 via a screw fastening a foot at the end of each of the arms 422, 424 to respective end portions of the second bracket portion 430. Advantageously, this allows dismantling of the bracket and easy removal and replacement of the leaf actuators 254 for maintenance and repair.

As shown in FIG. 4, the rotatable part 254 is formed as a tube with a threaded part on the interior surface. The rotatable part 254 attached to the motor 258 features a series of machined slots 262 which facilitate a flexible coupling system between the leaf actuator motor output shaft and rotatable part 254. The machined slots are patterned such that the rotatable part 254 remains integrally formed as a single piece component because no one slot runs around the entire circumference of the rotatable part 254. The machined slots are provided through the wall of the rotatable part 254 to each extend around a portion of the circumference of the rotatable part 254. The slots are offset from each other in the direction of the axis of the rotatable part 254 and the start and end position of any one slot are offset from those of the around the circumferential direction of the rotatable part 254. This provides some flexibility in the connection between the motor output shaft and the rotatable part 254. The slots allow bending of the rotatable part so that its axis is no longer completely parallel to (i.e. forms an acute angle with) the axis of the motor output shaft. Advantageously, small misalignments between the leaf actuator motor mounting and leaf/leaf actuator screw can be accommodated.

The leaf actuator screw can be made from any solid material. Particularly suitable materials are those having low corrosion low wear, high strength and/or low density. Materials which are light and stiff are most suitable. For example, the leaf actuator screw material can be aluminium, steel, titanium or any alloys thereof, or a composite material such as carbon fibre composite.

Control of the Actuators

A suitable controller will typically be provided (not shown), which is arranged to provide signals to the leaf actuators 250 in order to move the appropriate leaf or leaves 252 to provide the required shape or position of the aperture. As the person skilled in the art will appreciate, the leaf actuators 254, in particular the leaf actuator motors 258, are connected to suitable drives for converting step, speed and/or direction input from the controller to actuator currents and voltages.

In the above implementations, the motors are aligned with the line of movement which they are driving. This is design is known as a "direct drive".

Advantages

Advantageously, the leaf unit according to embodiments allows for a high leaf speed because the leaf actuator screw is rotationally static. Therefore, vibration of the leaf actuator screw due to revolutions thereof is eliminated. The leaf actuator screw can still be manufactured to fit within the width of the leaf as no increase to the diameter thereof is required to maintain stability. The rotatable part can have a larger diameter than that of the leaf actuator screw, because it is not as constrained by the thickness of the individual leaves. The rotatable part has a higher critical speed than the leaf actuator screw due to the larger diameter. Therefore, the rotatable part can operate at higher rotational speeds than the leaf actuator screw without reaching its critical speed and causing damage due to vibrations.

The higher rotational speed of the rotatable part directly translates to a higher linear speed of the leaf. Thus, for the same leaf actuator screw pitch, higher leaf speed is possible without compromising on stability and durability of the leaf actuator. Therefore, the advantages of a low pitch leadscrew, (improved positioning performance and self-locking) can be encompassed into the leaf actuator design. The leaf actuator can have high rotational speed and thus provided a high leaf speed, without the limiting factors previously discussed.

The disclosed leaf unit design allows faster leaf speeds without suffering from the aforementioned difficulties with vibration, leaf position accuracy or control system complexity. The alternative design has all the advantages of the direct-drive leaf actuator design but avoids the associated problems of reaching critical speeds and overhauling of leadscrews.

Therefore, in embodiments, the leaf actuator provides a fast, accurate and reliable change in aperture shape and/or position. Thus, during treatment, the radiation dose provided to the target tissue can be maximised while the dose applied to healthy tissue surrounding the target tissue can be minimised, even if the patient, and hence the tumour, is moving.

There is presented a multi-leaf collimator, or a beam limiting device, for limiting a beam of radiation. The multi-leaf collimator comprises a leaf, the beam limiting device comprising any of the multi-leaf collimators described herein. There is also presented a radiotherapy device comprising said beam limiting device.

There is also provided a method of driving leaves of the multi-leaf collimators described herein, the method comprising driving the leaf actuators to engender relative linear motion between the leaves in at least one leaf bank.

It may be understood that when the terms 'parallel', 'perpendicular' or 'in the plane of' are used to describe the relative arrangement of features and components, small deviations therefrom are permitted provided that they do not affect the functional and/or operational aspects of the multi-leaf collimator modules described herein.

Features of the above aspects can be combined in any suitable manner. It will be understood that the above description is of specific embodiments by way of aspect only and that many modifications and alterations will be within the skilled person's reach and are intended to be covered by the scope of the appendant claims.

The invention claimed is:

1. A leaf unit assembly for a multi-leaf collimator, the leaf unit assembly comprising:
    a leaf;
    a leaf actuator screw having a first end fixedly attached to the leaf;
    a rotatable part threadably engaged with the leaf actuator screw;
    a leaf actuator motor coupled to the rotatable part; and
    a support bracket comprising:
        a first portion comprising a first opening arranged to receive and support the leaf actuator motor; and
        a second portion comprising a second opening having a bearing therein, arranged to receive and support the rotatable part, wherein a center of the first opening is aligned with that of the second opening so that an axis of the leaf actuator motor and an axis of the rotatable part of each leaf actuator are collinear.

2. The leaf unit assembly according to claim 1, wherein the first end of the leaf actuator screw is coupled to the leaf so as to prevent relative rotational motion between the leaf and the leaf actuator screw around an axis of the leaf actuator screw.

3. The leaf unit assembly according to claim 1, wherein the leaf actuator screw has a second end opposite the first end, wherein the rotatable part is a tube that envelops at least a portion of the second end of the leaf actuator screw.

4. The leaf unit assembly according to claim 1, wherein, upon rotation of the rotatable part relative to the leaf, the rotatable part is configured to cause a relative linear motion between itself and the leaf.

5. The leaf unit assembly according to claim 1, wherein the leaf actuator screw is configured to move between an extended position in which over half of the leaf actuator screw is outside the rotatable part, and a retracted position in which over half of the leaf actuator screw is enveloped by the rotatable part.

6. The leaf unit assembly according to claim 1, wherein the rotatable part comprises a plurality of slots, wherein each slot of the plurality of slots extend around a portion of a circumference of the rotatable part, and wherein each slot of the plurality of slots are offset from each other in a direction of an axis of the rotatable part.

7. The leaf unit assembly according to claim 1, wherein the rotatable part has a first end threadably engaged with the leaf actuator screw and a second end coupled to the leaf actuator motor.

8. The leaf unit assembly according to claim 1, wherein the leaf actuator screw has at least one of a diameter of up to 2 mm or a length of at least 100 mm.

9. A multi-leaf collimator for a radiotherapy device, the multi-leaf collimator comprising:

a leaf bank including a plurality of leaf unit assemblies wherein each leaf unit assembly of the plurality the leaf unit assemblies comprises:
    a leaf,
    a leaf actuator screw having a first end fixedly attached to the leaf, and
    a rotatable part threadably engaged with the leaf actuator screw;
    a leaf actuator motor coupled to the rotatable part; and
    a support bracket comprising:
        a first portion comprising a first opening arranged to receive and support the leaf actuator motor; and
        a second portion comprising a second opening having a bearing therein, arranged to receive and support the rotatable part, wherein a center of the first opening is aligned with that of the second opening so that an axis of the leaf actuator motor and an axis of the rotatable part of each leaf actuator are collinear, and wherein a rotational movement of each leaf relative to each other is restricted such that rotation of each rotatable part imparts linear motion of the respective leaf actuator screw and leaf relative to the rotatable part.

10. The multi-leaf collimator according to claim 9, wherein the rotatable part of each leaf unit assembly is operable to move a respective leaf in a linear motion independently of any other leaf in the leaf bank.

11. The multi-leaf collimator according to claim 9, wherein the first portion is removably attached to the second portion.

12. A radiotherapy device comprising:
    a multi-leaf collimator, the multi-leaf collimator comprising:
        a leaf bank including one or more leaf assembly units, wherein each of the one or more leaf assembly units comprises:
            a leaf;
            a leaf actuator screw having a first end fixedly attached to the leaf;
            a rotatable part threadably engaged with the leaf actuator screw;
            a leaf actuator motor coupled to the rotatable part; and
            a support bracket comprising:
                a first portion comprising a first opening arranged to receive and support the leaf actuator motor; and
                a second portion comprising a second opening having a bearing therein, arranged to receive and support the rotatable part, wherein a center of the first opening is aligned with that of the second opening so that an axis of the leaf actuator motor and an axis of the rotatable part of each leaf actuator are collinear.

13. The radiotherapy device of claim 12, wherein a rotational movement of each leaf relative to each other is restricted such that rotation of each rotatable part causes linear motion of the respective leaf actuator screw and leaf relative to the rotatable part.

14. The radiotherapy device of claim 12, wherein the rotatable part of each leaf unit assembly is operable to move a respective leaf in a linear motion independently of any other leaf in the leaf bank.

* * * * *